US012076453B2

(12) United States Patent
Miller et al.

(10) Patent No.: US 12,076,453 B2
(45) Date of Patent: Sep. 3, 2024

(54) PORTABLE UV SANITIZATION DEVICE

(71) Applicant: Prostar Technologies, Inc., New York, NY (US)

(72) Inventors: Michael Alan Miller, Winter Garden, FL (US); Fredric Maxik, Cocoa Beach, FL (US); Todd Brinley Sampson, Orlando, FL (US); Ran Zhou, Rockledge, FL (US)

(73) Assignee: Prostar Technologies, Inc., New York, NY (US)

( * ) Notice: Subject to any disclaimer, the term of this patent is extended or adjusted under 35 U.S.C. 154(b) by 483 days.

(21) Appl. No.: 17/404,275

(22) Filed: Aug. 17, 2021

(65) Prior Publication Data

US 2022/0047743 A1    Feb. 17, 2022

Related U.S. Application Data

(60) Provisional application No. 63/066,590, filed on Aug. 17, 2020.

(51) Int. Cl.
*A61L 2/10*          (2006.01)

(52) U.S. Cl.
CPC .............. *A61L 2/10* (2013.01); *A61L 2202/11* (2013.01); *A61L 2202/121* (2013.01); *A61L 2202/16* (2013.01)

(58) Field of Classification Search
CPC .. A61L 2/10; A61L 2202/11; A61L 2202/121; A61L 2202/16; A61L 2202/25
See application file for complete search history.

(56) References Cited

U.S. PATENT DOCUMENTS

| 5,029,252 | A  | 7/1991  | Ameseder |
| 7,282,728 | B2 | 10/2007 | Culbert |
| 7,612,492 | B2 | 11/2009 | Lestician |
| 7,794,673 | B2 | 9/2010  | Lucas et al. |
| 7,824,065 | B2 | 11/2010 | Maxik |
| 8,097,861 | B2 | 1/2012  | Leben |
| 8,201,968 | B2 | 6/2012  | Maxik et al. |
| 8,672,518 | B2 | 3/2014  | Boomgaarden et al. |

(Continued)

FOREIGN PATENT DOCUMENTS

| BR | 102016015623 A2 | 2/2018 |
| CH | 714094 A2       | 3/2019 |

(Continued)

*Primary Examiner* — David A Vanore
(74) *Attorney, Agent, or Firm* — Vierra Magen Marcus LLP

(57) ABSTRACT

A portable ultraviolet sanitization device is disclosed that includes a gripping portion, an ultraviolet electromagnetic radiation emitter portion, and a power source. The ultraviolet electromagnetic radiation emitter portion is disposed at a distal end of the gripping portion. The ultraviolet electromagnetic radiation emitter portion includes one or more ultraviolet light sources, such as light emitting diodes or excimer lamps. The power source is in electrical connection with the one or more ultraviolet light sources. The sanitization device is used to sanitize surfaces by eliminating viruses and other microorganisms. The sanitization device is particularly well-equipped to sanitize surfaces that are used intermittently, such as airplane cabins, restaurant seating areas, or similarly occupied spaces.

13 Claims, 3 Drawing Sheets

(56) References Cited

U.S. PATENT DOCUMENTS

| | | |
|---|---|---|
| 8,877,124 B2 | 11/2014 | Bergman |
| 8,967,844 B2 | 3/2015 | Boomgaarden et al. |
| 8,975,605 B2 | 3/2015 | Neister |
| 9,358,313 B2 | 6/2016 | Deal |
| 9,370,600 B1 | 6/2016 | DuPuis et al. |
| 9,511,163 B2 | 12/2016 | Larsen |
| 9,517,280 B2 | 12/2016 | Lynn et al. |
| 9,597,420 B2 | 3/2017 | Maxik et al. |
| 9,648,284 B2 | 5/2017 | Holland et al. |
| 9,681,108 B2 | 6/2017 | Holland et al. |
| 9,726,365 B1 | 8/2017 | Maxik et al. |
| 9,739,470 B2 | 8/2017 | Boomgaarden et al. |
| 9,839,707 B2 * | 12/2017 | Won ................... A61L 2/10 |
| 9,855,353 B1 | 1/2018 | Stacy |
| 9,907,870 B2 | 3/2018 | Boodaghians et al. |
| 9,956,306 B2 | 5/2018 | Brais et al. |
| 9,981,052 B2 | 5/2018 | Clynne et al. |
| 10,072,835 B2 | 9/2018 | Maxik et al. |
| 10,105,460 B1 | 10/2018 | Collins et al. |
| 10,124,081 B2 | 11/2018 | Agafonov et al. |
| 10,228,622 B2 | 3/2019 | Kimsey-Lin |
| 10,265,428 B1 | 4/2019 | Gross et al. |
| 10,301,806 B2 | 5/2019 | Childress et al. |
| 10,322,204 B2 | 6/2019 | He |
| 10,354,857 B2 | 7/2019 | Chen et al. |
| 10,363,327 B2 | 7/2019 | Liao et al. |
| 10,517,976 B2 | 12/2019 | Shur et al. |
| 10,576,174 B2 | 3/2020 | Shur et al. |
| 10,624,979 B2 | 4/2020 | Brockschmidt et al. |
| 10,641,476 B2 | 5/2020 | Maxik et al. |
| 10,688,211 B2 | 6/2020 | Barber, III |
| 2002/0074559 A1 | 6/2002 | Dowling et al. |
| 2004/0208798 A1 * | 10/2004 | Splane, Jr. ............ F24F 8/192 422/4 |
| 2007/0086912 A1 | 4/2007 | Dowling et al. |
| 2015/0074887 A1 | 3/2015 | Theuerl et al. |
| 2015/0284266 A1 | 10/2015 | Matsui |
| 2017/0164719 A1 * | 6/2017 | Wheeler ............... A45D 42/10 |
| 2018/0207302 A1 | 7/2018 | Vasilenko |
| 2019/0160192 A1 | 5/2019 | Fudakowski |
| 2019/0192709 A1 | 6/2019 | Igarashi |
| 2019/0192710 A1 | 6/2019 | Andersson et al. |
| 2019/0249847 A1 | 8/2019 | Hallack et al. |
| 2019/0255201 A1 * | 8/2019 | Rosen ................ A61L 2/0052 |
| 2019/0298869 A1 | 10/2019 | Poulsen |
| 2019/0365938 A1 | 12/2019 | Romo et al. |
| 2020/0038542 A1 | 2/2020 | Franklin et al. |
| 2020/0101183 A1 | 4/2020 | Dijkstra et al. |
| 2020/0147249 A1 | 5/2020 | Hussein et al. |
| 2020/0188542 A1 | 6/2020 | Lei et al. |
| 2020/0215214 A1 * | 7/2020 | Rosen ................ A61L 2/084 |
| 2021/0346561 A1 * | 11/2021 | Callahan ............... A61L 2/28 |
| 2021/0369887 A1 * | 12/2021 | Mehandjiysky ........ A61L 2/10 |

FOREIGN PATENT DOCUMENTS

| | | |
|---|---|---|
| EP | 2095830 A1 | 9/2009 |
| EP | 3237857 A1 | 11/2017 |
| WO | 2005082426 A1 | 9/2005 |
| WO | 2018101943 A1 | 6/2018 |
| WO | 2019143699 A1 | 7/2019 |

\* cited by examiner

PORTABLE UV SANITIZATION DEVICE

CROSS-REFERENCE TO RELATED APPLICATIONS

This application claims the benefit of priority to U.S. Provisional Application Ser. No. 63/066,590 entitled "Portable UV Sanitization Device," filed Aug. 17, 2020, which is incorporated herein by reference in its entirety.

TECHNICAL FIELD

The present disclosure relates generally to a system including a portable, wand-shaped device used to provide ultraviolet light to a surface. More particularly, the portable, wand-shaped device may provide ultraviolet light to a surface for the purpose of sanitization.

BACKGROUND

The impact of the spread of viruses has been acutely felt throughout the world in the present time. COVID-19, SARS, and other viruses and microorganisms have had a significant and deadly impact on the way that individuals live their lives. In particular, individuals are less willing and/or able to occupy public spaces, such as airplanes, malls, restaurants, or the like, for fear of being exposed to and succumbing to a virus.

In order to combat the spread of viruses in public spaces, sanitization products have been applied. Standard sanitization products include aerosol sprays and cleaning solutions, which are applied by custodial or other staff members in between access to particular locations or use of a particular item in a public space. However, such sanitization products can have an effect on the environment through the increase use and preparation of chemical substances.

More recently, ultraviolet light has been introduced as a means to sanitize surfaces and substances. The type of ultraviolet (UV) light has been classified into at least four bands depending upon the effects upon the skin of humans and other animals. Such bands include UV-A, which is defined as ultraviolet light having a wavelength in a range from 315 nm to 400 nm; UV-B, which is defined as ultraviolet light having a wavelength in a range from 280 nm to 315 nm; UV-C, which is defined as ultraviolet light having a wavelength that is in a range from 235 nm to 280 nm; and Far UV, which is defined as ultraviolet light having a wavelength that is in a range from 185 nm to 235 nm.

Ultraviolet light in the UV-C range has been used for sanitization. For example, UV light emitted at 254 nm and 265 nm has been used to destroy viruses and other microorganisms for a number of years. However, UV light emitted in the UV-C range can have harmful impacts on humans. For example, prolonged direct exposure to UV-C light can result in eye and skin damage, such as acute corneal injury (sometimes referred to as "welder's eye") and acute erythema. Acute effects from UV-C light include redness, ulceration or burns of the skin. Longer-term effects may include premature aging of the skin and/or skin cancer. In contrast, Far UV light has been shown to not penetrate the human dermis or cause damage to the human eye while retaining sanitization effects.

As such, it would be desirable to have a Far UV light sanitization system that could be used by and/or in the presence of humans.

It would be further desirable to include a portable sanitization system that could be operated by a user to sanitize a plurality of surfaces in an enclosed space, such as an airplane cabin, a portion of a restaurant, or the like, without causing a deleterious impact to the health of the user or surrounding individuals.

SUMMARY

A portable sanitization device is provided. The portable sanitization device comprises a gripping portion, an ultraviolet electromagnetic radiation emitter portion, and a power source. The gripping portion has a proximal end, a distal end, and an interior. The UV EMR emitter portion is disposed at the distal end of the gripping portion and comprises one or more UV light sources. The UV EMR emitter portion also comprises an interior and an exterior. The power source is in electrical connection with the one or more UV light sources.

According some embodiments, the gripping portion comprises a handle and/or a hand guard.

According some embodiments, the one or more UV light sources are configured to emit UV light having a wavelength between 185 nm and 235 nm. According some embodiments, the one or more UV light sources are configured to emit UV light having a wavelength between 217 nm and 227 nm. According some embodiments, the one or more UV light sources are configured to emit UV light having a wavelength of 222 nm.

According some embodiments, the one or more UV light sources comprise one or more light emitting diodes (LEDs). According some embodiments, the one or more UV light sources comprise one or more excimer lamps.

According some embodiments, at least one of the one or more UV light sources is disposed within the interior of the UV EMR emitter portion. According some embodiments, at least one of the one or more UV light sources is disposed on the exterior of the UV EMR emitter portion.

According some embodiments, the exterior of the UV EMR emitter portion comprises a back shield configured to prevent UV EMR from passing therethrough. In some embodiments, the back shield comprises one or more reflective panels disposed adjacent to an aperture in the back shield. In some embodiments, the aperture is configured to permit UV EMR to pass therethrough. In some embodiments, the one or more reflective panels are configured to reflect at least a portion of the UV EMR passing through the aperture. According additional embodiments, the back shield of the UV EMR emitter portion is configured to be rotatable with respect to the gripping portion. According further embodiments, the sanitization device further comprises a servo motor and a rotational actuator. In some embodiments, the servo motor is configured to cause the back shield to rotate with respect to the gripping portion in response to the rotational actuator being actuated.

According some embodiments, the power source comprises a battery pack connected to the proximal end of the gripping portion. According some embodiments, the power source comprises a battery disposed within the interior of the gripping portion. According some embodiments, the power source is disposed within a backpack configured to be worn by a user. According some embodiments, the power source comprises a power cord configured to electrically connect the UV sanitization device to a remote source of power.

According some embodiments, the sanitization device further comprises a wire configured to electrically connect the power source to the one or more UV light sources and disposed at least in part within the interior of the gripping portion.

According some embodiments, the sanitization device further comprises a telescoping portion configured to cause the UV EMR emitter portion to be moved axially in relation to the gripping portion. According additional embodiments, the sanitization device further comprises a servo motor and a telescoping actuator. In some embodiments, the servo motor is configured to cause the telescoping portion to move the UV EMR emitter portion axially with respect to the gripping portion in response to the telescoping actuator being actuated.

BRIEF DESCRIPTION OF THE DRAWINGS

The accompanying drawings, which are incorporated in and form a part of the specification, illustrate the embodiments of the invention and together with the written description serve to explain the principles, characteristics, and features of the invention. In the drawings.

DETAILED DESCRIPTION

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

The embodiments of the present teachings described below are not intended to be exhaustive or to limit the teachings to the precise forms disclosed in the following detailed description. Rather, the embodiments are chosen and described so that others skilled in the art may appreciate and understand the principles and practices of the present teachings.

Figure 1:
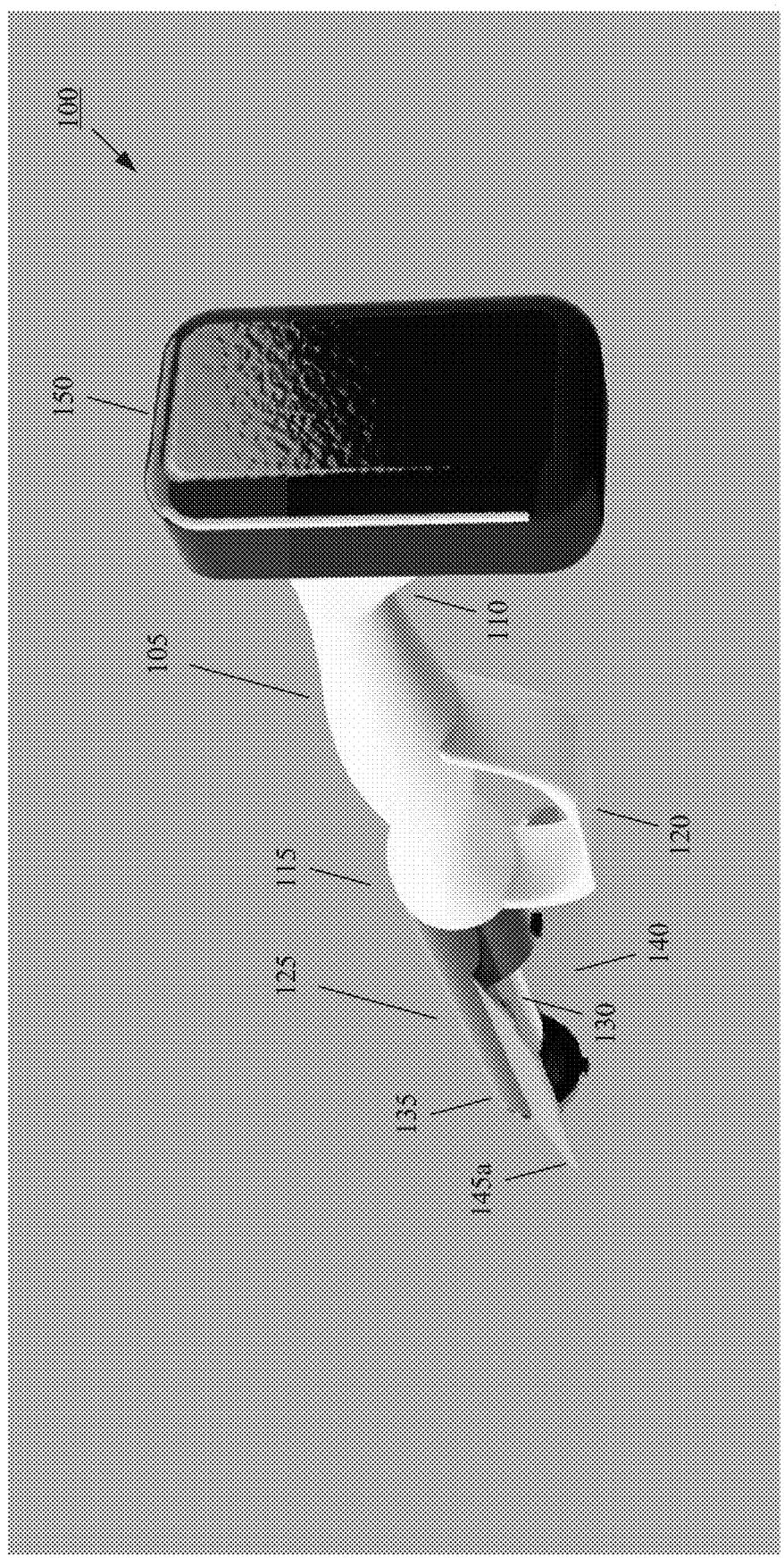
FIG. 1 depicts an illustrative portable UV sanitization device in accordance with an embodiment.
Figure 2:
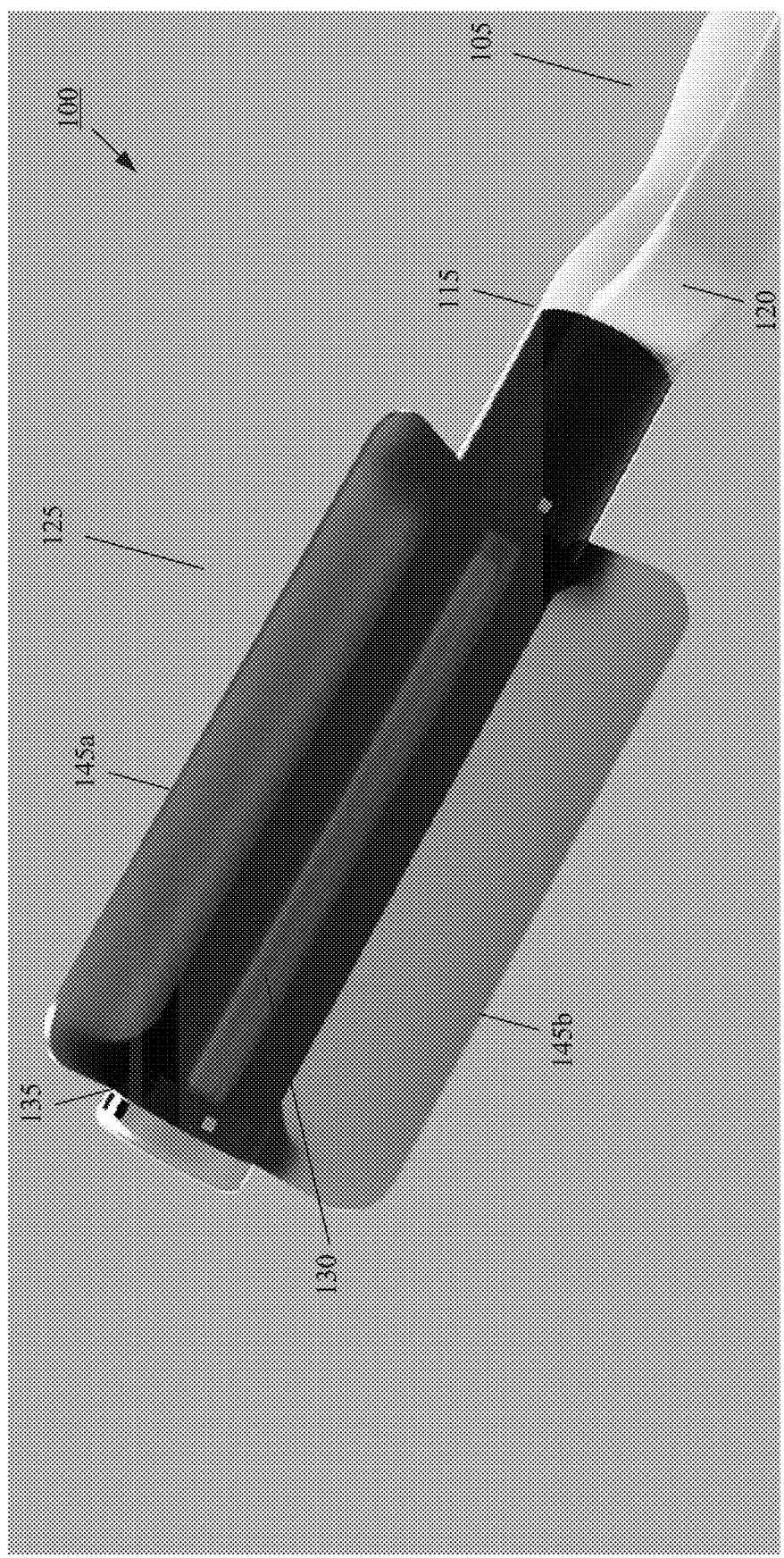
FIG. 2 depicts a UV EMR emitter portion of a portable UV sanitization device in accordance with an embodiment.
Figure 3:
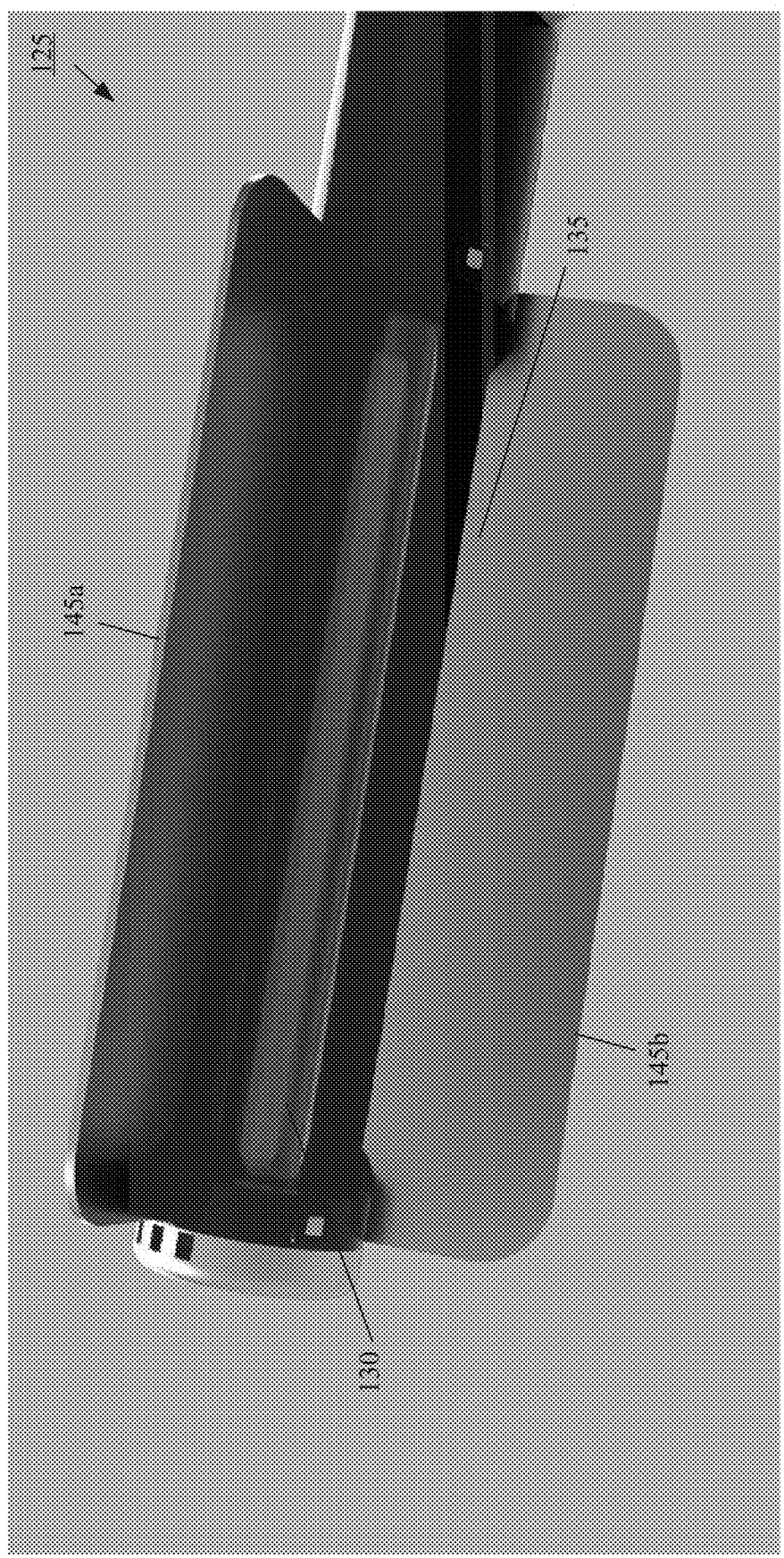
FIG. 3 depicts a UV light source and back shield of a UV sanitization device in accordance with an embodiment.

FIG. 1 depicts an illustrative portable UV sanitization device in accordance with an embodiment. FIG. 2 depicts a UV EMR emitter portion of a portable UV sanitization device in accordance with an embodiment. FIG. 3 depicts a UV light source and back shield of a UV sanitization device in accordance with an embodiment. Similar features within FIGS. 1-3 are identified with common reference numbers.

As shown in FIGS. 1-3, the portable UV sanitization device 100 comprises a gripping portion 105, an ultraviolet (UV) electromagnetic radiation (EMR) emitter portion 125, and a power source 150.

The gripping portion 105 may include a proximal end 110 and a distal end 115. The gripping portion 105 may further have an interior and an exterior. In some embodiments, the interior of the gripping portion 105 may be substantially hollow. In some embodiments, the interior of the gripping portion 105 may be configured to house one or more components of the portable UV sanitization device 100. In some embodiments, the gripping portion 105 may include a handle and/or a hand guard 120 configured to enable a user to more securely and/or comfortably hold the gripping portion when in use.

The ultraviolet (UV) electromagnetic radiation (EMR) emitter portion 125 may be disposed at the distal end 115 of the gripping portion 105. The UV EMR emitter portion 125 may be configured to emit UV EMR when operated. In some embodiments, the UV EMR emitter portion 125 may be configured to emit UV EMR having a wavelength in the Far UV range (i.e., between about 185 nm and about 235 nm). In some embodiments, the UV EMR emitter portion 125 may be configured to emit UV EMR having a wavelength of 222 nm. Additional or alternate wavelengths of EMR may also be emitted by the UV EMR emitter portion 125 including, for example and without limitation, one or more wavelengths of visible light (between about 380 nm and about 740 nm).

The UV EMR emitter portion 125 may include one or more UV light sources, such as 130. In some embodiments, the one or more UV light sources 130 comprise one or more UV light emitting diodes (LEDs). In some embodiments, the one or more UV light sources 130 comprise one or more excimer lamps. In some embodiments, the UV EMR emitter portion may further include one or more additional light sources, such as an incandescent light source, a fluorescent light source, a LED light source or the like that emit visible light. Additional or alternate types of UV light sources 130 and/or additional light sources may also be used as will be apparent to those of ordinary skill in the related art based on the teachings of this disclosure.

In some embodiments, at least one of the one or more UV light sources 130 may be disposed within the interior of the UV EMR emitter portion 125. In some embodiments, the exterior of the UV EMR emitter portion 125 may include a back shield 135 configured to prevent UV EMR from passing therethrough. The back shield 135 may be configured to form an aperture 140 through which UV EMR may pass when the UV sanitization device is in operation. The back shield 135 may include one or more UV reflective panels 145a, 145b disposed adjacent to the aperture 140. The one or more reflective panels 145a, 145b may be configured to reflect UV EMR directed toward the one or more reflective panels in a direction coincident with the aperture 140.

In some embodiments, the interior of the back shield 135 and the reflective panels 145a, 145b may each be coated with a reflective material. For example, and without limitation, the reflective material may include one or more of Mylar®, titanium dioxide ($TiO_2$), expanded polytetrafluoroethylene (e-PTFE), and aluminum. Additional or alternate reflective materials will be apparent to those of ordinary skill in the related art based on the teachings of this disclosure.

In some embodiments, the back shield 140 and the reflective panels 145a, 145b may be configured to be rotated with respect to the gripping portion 105. Rotating the back shield 140 and the reflective panels 145a, 145b may enable UV EMR to be emitted from the one or more UV light sources 130 in any of a plurality of directions while maintaining a position of the gripping portion 105.

In some embodiments, the UV sanitization device 100 may include a servo motor (not shown) and a rotational actuator (not shown). The servo motor may be disposed, for example and without limitation, within the interior of the gripping portion 105. In some embodiments, the servo motor may be disposed at a distal end 115 of the gripping portion 105 in proximity to the UV EMR emitter portion 125. The rotational actuator may include one or more of a push button, a push switch, a sliding switch, a sensor, or any other mechanism used to mechanically or electrically signal initiation or cessation of an operation. For example, the servo motor may be used to cause the rotation of the back shield 140 and the reflective panels 145*a*, 145*b* with respect to the gripping portion 105 in response to the rotational actuator being actuated.

In some embodiments, at least one of the one or more UV light sources 130 may be located on the exterior of the UV EMR emitter portion 125. For example, the UV EMR emitter portion 125 may comprise one or more holes (not shown) through which one or more UV LED light sources 130 are disposed. Additional and alternate methods of disposing the one or more UV light sources will be apparent to those of ordinary skill in the related art based on the teachings of this disclosure.

In some embodiments, the UV EMR emitter portion 125 may be configured to be rotated with respect to the gripping portion 105. Rotating the UV EMR emitter portion 125 may enable UV EMR to be emitted from the one or more UV light sources 130 in any of a plurality of directions while maintaining a position of the gripping portion 105.

In some embodiments, the UV sanitization device 100 may include a servo motor (not shown) and a rotational actuator (not shown). The servo motor may be disposed, for example and without limitation, within the interior of the gripping portion 105. In some embodiments, the servo motor may be disposed at a distal end 115 of the gripping portion 105 in proximity to the UV EMR emitter portion 125. The rotational actuator may include one or more of a push button, a push switch, a sliding switch, a sensor, or any other mechanism used to mechanically or electrically signal initiation or cessation of an operation. For example, the servo motor may be used to cause the rotation of the UV EMR emitter portion 125 and thereby rotation of the one or more UV light sources 130 with respect to the gripping portion 105 in response to the rotational actuator being actuated.

As stated above, the UV sanitization device 100 may include a power source, such as 150. As shown in FIG. 1, the power source may include a battery pack 150. The battery pack 150 may be connected to, for example and without limitation, the proximal end 110 of the gripping portion 105 via a standard connection known to those of ordinary skill in the related art. In an alternate embodiment, the power source 150 may include a battery disposed within the interior of the gripping portion 105. In yet another embodiment, the power source 150 may be disposed within a backpack (not shown) configured to be worn by a user. In such an embodiment, an electrical connection may be used to connect the power source 150 to the UV sanitization device 100. For example, the electrical connection may comprise a power cord (not shown) configured to be plugged into or otherwise connected to the UV sanitization device 100 through the proximal end 110 of the gripping portion 105. In an alternate embodiment, the power source 150 may comprise a power cord (not shown) that is integral to the UV sanitization device 100 and configured to connect to a remote source of power via a plug or other connector at a remote end of the cable.

In an embodiment, the UV sanitization device 100 may further include a telescoping portion (not shown). The telescoping portion may be configured to cause the UV EMR emitter portion 125 to be moved axially in relation to the gripping portion 105. In some embodiments, the telescoping portion may be disposed at or near an abutment of the UV EMR emitter portion 125 and the gripping portion 105. For example, the telescoping portion may be disposed at least in part within an interior of the gripping portion 105 and in abutment with a proximal end of the UV EMR emitter portion 125.

In some embodiments, the UV sanitization device 100 may include a servo motor (not shown) and a telescoping actuator (not shown). The servo motor may be disposed, for example and without limitation, within the interior of the gripping portion 105. In some embodiments, the servo motor may be disposed at or near a distal end 115 of the gripping portion 105 in proximity to the UV EMR emitter portion 125. The telescoping actuator may include one or more of a push button, a push switch, a sliding switch, a sensor, or any other mechanism used to mechanically or electrically signal initiation or cessation of an operation. For example, the servo motor may be used to cause the movement of the UV EMR emitter portion 125 towards or away from the gripping portion 105 in response to actuation of the telescoping actuator.

In operation, a user may hold the gripping portion of the UV sanitization device and provide power to the device by engaging the power source, such as by turning on a power switch. With the power engaged, the one or more UV light sources may be powered on. The UV sanitization device may be moved in proximity to a surface such that UV EMR from the one or more UV light sources is directed towards the surface. The wavelength of the UV EMR from the one or more UV light sources may be selected to be useful in destroying or otherwise neutralizing microorganisms, such as viruses, while being harmless to humans. In some embodiments, the wavelength of the UV EMR may be within a range from 185 nm to 235 nm. In some embodiments, the wavelength of the UV EMR may be 222 nm.

The UV sanitization device may be used, for example and without limitation to sanitize an area used by different people over time. For example, the UV sanitization device may be used to sanitize an airplane cabin in between flights, a restaurant table setting in between patrons, a conference room in between meetings, or the like. The UV sanitization device is designed to be portable and light enough to be used by an individual without causing strain to the user's joints or back. In some embodiments, the UV sterilization device may be stored in a holster on the user's waist when not in use. In some embodiments, the UV sterilization device may be stored in a backpack, such as the one described above that includes a power supply, when not in use.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A portable sanitization device comprising:
   a gripping portion having a proximal end, a distal end, and an interior;
   an ultraviolet (UV) electromagnetic radiation (EMR) emitter portion disposed at the distal end of the gripping portion, wherein the UV EMR emitter portion comprises one or more UV light sources, wherein the UV EMR emitter portion comprises an interior and an exterior, wherein the exterior of the UV EMR emitter portion comprises a back shield configured to prevent UV EMR from passing therethrough, wherein the back shield comprises one or more reflective panels disposed adjacent to an aperture in the back shield, wherein the aperture is configured to permit UV EMR to pass therethrough, wherein the one or more reflective panels are configured to reflect at least a portion of the UV EMR passing through the aperture; and
   a power source in electrical connection with the one or more UV light sources.

2. The sanitization device of claim 1, wherein the gripping portion comprises one or more of a handle and a hand guard.

3. The sanitization device of claim 1, wherein the one or more UV light sources are configured to emit UV light having a wavelength between 185 nm and 235 nm.

4. The sanitization device of claim 1, wherein the one or more UV light sources are configured to emit UV light having a wavelength between 217 nm and 227 nm.

5. The sanitization device of claim 1, wherein the one or more UV light sources are configured to emit UV light having a wavelength of 222 nm.

6. The sanitization device of claim 1, wherein the one or more UV light sources comprise one or more light emitting diodes (LEDs).

7. The sanitization device of claim 1, wherein the one or more UV light sources comprise one or more excimer lamps.

8. The sanitization device of claim 1, wherein at least one of the one or more UV light sources is disposed within the interior of the UV EMR emitter portion.

9. The sanitization device of claim 1, wherein at least one of the one or more UV light sources is disposed on the exterior of the UV EMR emitter portion.

10. The sanitization device of claim 1, wherein the power source comprises a battery pack connected to the proximal end of the gripping portion.

11. The sanitization device of claim 1, wherein the power source comprises a battery disposed within the interior of the gripping portion.

12. The sanitization device of claim 1, further comprising a wire configured to electrically connect the power source to the one or more UV light sources and disposed at least in part within the interior of the gripping portion.

13. A portable sanitization device comprising:
    a gripping portion having a proximal end, a distal end, and an interior;
    an ultraviolet (UV) electromagnetic radiation (EMR) emitter portion disposed at the distal end of the gripping portion, wherein the UV EMR emitter portion comprises one or more UV light sources, wherein the UV EMR emitter portion comprises an interior and an exterior;
    a power source in electrical connection with the one or more UV light sources; and
    a telescoping portion configured to cause the UV EMR emitter portion to be moved axially in relation to the gripping portion.

* * * * *